US006799966B1

(12) United States Patent
Horn et al.

(10) Patent No.: US 6,799,966 B1
(45) Date of Patent: Oct. 5, 2004

(54) FLUOROPOLYMERIC ORTHODONTIC ARTICLE

(75) Inventors: Jerold S. Horn, Los Angeles, CA (US); James D. Hansen, Pasadena, CA (US)

(73) Assignee: 3M Innovative Properties Company, St. Paul, MN (US)

(*) Notice: Subject to any disclaimer, the term of this patent is extended or adjusted under 35 U.S.C. 154(b) by 0 days.

(21) Appl. No.: 09/262,628

(22) Filed: Mar. 4, 1999

(51) Int. Cl.[7] .............................................. A61C 3/00
(52) U.S. Cl. .............................. 433/8; 433/9; 433/10; 433/11; 433/12; 433/13; 433/14; 433/15; 433/16; 433/17
(58) Field of Search ........................... 433/8, 9, 10, 11, 433/12, 13, 14, 15, 16, 17

(56) References Cited

U.S. PATENT DOCUMENTS

| | | | |
|---|---|---|---|
| 3,504,438 A | * | 4/1970 | Wittman |
| 3,527,737 A | | 9/1970 | Masuhara et al. ......... 260/78.5 |
| 3,545,083 A | | 12/1970 | Krasne |
| 3,589,010 A | | 6/1971 | Taniguchi ........................ 32/2 |
| 3,712,877 A | * | 1/1973 | Patel |
| 3,765,091 A | | 10/1973 | Northcutt ..................... 32/14 A |
| 3,775,850 A | | 12/1973 | Northcutt ..................... 32/14 A |
| 3,829,973 A | | 8/1974 | Masuhara et al. ............. 32/15 |
| 3,889,374 A | | 6/1975 | Saffir ................................. 32/2 |
| 3,922,787 A | | 12/1975 | Fischer et al. .............. 32/14 A |
| 3,930,311 A | | 1/1976 | Andrews .................... 32/14 A |
| 3,964,165 A | | 6/1976 | Stahl .......................... 32/14 A |
| 4,035,565 A | * | 7/1977 | Apotheker .................. 526/249 |
| 4,050,156 A | | 9/1977 | Chasanoff et al. ............... 32/2 |
| 4,064,311 A | | 12/1977 | McLean et al. .............. 428/434 |
| 4,080,357 A | | 3/1978 | Gergen et al. ........... 260/42.18 |
| 4,088,627 A | | 5/1978 | Gergen et al. ........... 260/42.18 |
| 4,107,131 A | | 8/1978 | Gergen et al. .......... 260/40 TN |
| 4,111,894 A | | 9/1978 | Gergen et al. ............ 260/40 R |
| 4,111,895 A | | 9/1978 | Gergen et al. ........... 260/42.18 |
| 4,180,911 A | | 1/1980 | Bullock ......................... 433/9 |
| 4,204,325 A | | 5/1980 | Kaelble ......................... 433/9 |
| 4,222,128 A | | 9/1980 | Tomonaga et al. .............. 3/1.9 |
| 4,323,956 A | * | 4/1982 | Pustka ........................ 362/374 |
| 4,413,094 A | | 11/1983 | Aufdermarsh, Jr. ......... 525/187 |
| 4,431,420 A | | 2/1984 | Adair ......................... 433/199 |
| 4,451,235 A | | 5/1984 | Okuda et al. .............. 433/201 |
| 4,668,193 A | | 5/1987 | Burgess et al. .......... 433/222.1 |
| 4,712,999 A | | 12/1987 | Rosenberg ..................... 433/8 |
| 4,717,341 A | | 1/1988 | Goldberg et al. .............. 433/9 |
| 4,746,685 A | | 5/1988 | Masuhara et al. ............ 522/13 |
| 4,850,865 A | | 7/1989 | Napolitano ..................... 433/8 |
| 4,863,974 A | | 9/1989 | Mallouk et al. .............. 521/85 |
| 4,867,679 A | * | 9/1989 | Rackley ...................... 433/15 |
| 4,877,402 A | | 10/1989 | Hirabayashi et al. ....... 433/218 |
| 4,882,390 A | * | 11/1989 | Kolb ........................ 525/326.3 |
| 4,920,188 A | | 4/1990 | Sakashita et al. ........... 526/196 |
| 4,948,366 A | | 8/1990 | Horn et al. .................... 433/9 |
| 4,954,080 A | | 9/1990 | Kelly et al. .................... 433/8 |
| 4,985,516 A | | 1/1991 | Sakashita et al. ........... 526/196 |
| 5,008,135 A | | 4/1991 | Giordano et al. ........... 427/386 |
| 5,035,621 A | | 7/1991 | Gottschalk et al. ......... 433/226 |
| 5,123,844 A | | 6/1992 | Wakai et al. ............. 433/201.1 |
| 5,128,122 A | | 7/1992 | Cerami et al. ................ 424/49 |
| 5,164,187 A | | 11/1992 | Constantz et al. .......... 424/423 |
| 5,183,403 A | | 2/1993 | Masuhara et al. ............. 433/9 |
| 5,254,002 A | | 10/1993 | Reher et al. .................... 433/8 |
| 5,264,215 A | | 11/1993 | Nakabayashi et al. ...... 424/423 |
| 5,279,831 A | | 1/1994 | Constantz et al. .......... 424/423 |
| 5,310,835 A | | 5/1994 | Skoultchi et al. ........... 526/198 |
| 5,317,074 A | | 5/1994 | Hammar et al. .............. 528/44 |
| 5,322,613 A | | 6/1994 | Ohira ......................... 205/50 |
| 5,338,773 A | | 8/1994 | Lu et al. .................... 523/116 |
| 5,354,199 A | | 10/1994 | Jacobs et al. .................. 433/9 |
| 5,427,831 A | | 6/1995 | Stevens ..................... 428/36.2 |
| 5,443,511 A | | 8/1995 | Ogawa et al. ............... 623/16 |
| 5,454,716 A | | 10/1995 | Banerjee et al. ............. 433/20 |
| 5,461,133 A | * | 10/1995 | Hammar ..................... 528/10 |
| 5,539,070 A | | 7/1996 | Zharov et al. .............. 526/198 |
| 5,558,516 A | | 9/1996 | Horn et al. .................... 433/9 |
| 5,597,302 A | | 1/1997 | Pospisil et al. ................ 433/8 |
| 5,616,796 A | | 4/1997 | Pocius et al. .................. 564/9 |
| 5,681,910 A | | 10/1997 | Pocius ....................... 526/198 |
| 5,994,028 A | * | 11/1999 | Lee ......................... 430/273.1 |

FOREIGN PATENT DOCUMENTS

| | | |
|---|---|---|
| EP | 211408 | 2/1987 |
| GB | 1113722 | 5/1968 |
| GB | 2253420 | 9/1992 |
| JP | 61220646 | 9/1986 |
| JP | 5-246951 | 9/1993 |
| JP | 07089821 A | 4/1995 |
| WO | WO 95/22567 | 8/1995 |
| WO | WO 97/07151 | 2/1997 |
| WO | WO 97/07171 | 2/1997 |
| WO | WO 98/17694 | 4/1998 |

OTHER PUBLICATIONS

Whelan, T.,"Polymer Technology Dictionary", (1994), 161, Chapman & Hall, (New York).*
ASM Engineered Matls. Reference Book, "Fluoroplastics," pp. 298–299 (1989).
ASTM Test Method D 1003—92, "Standard Test Method for Haze and Luminous Transmittance of Transparent Plastics," pp. 235–239 (1992).
ASTM Test Method E 308—95, "Standard Practice for Computing the Colors of Objects by Using the CIE System," pp. 253–283 (1995).
Imai et al., "Importance of Polymerization initiator Systems and Interfacial Initiation of Polymerization in Adhesive Bonding of Resin to Dentin," J. Dent. Res., 70(7):1088–1091, Jul. 1991.
Kirk–Othmer, *Encyclopedia of Chemical Technology*, vol. 11, pp. 621–624, 644, 650–651, 657, 660, 671–672, 677, 683, 686, 694, 712–713, 719, 722, Fourth Edition (1992).

(List continued on next page.)

*Primary Examiner*—Bernard Lipman
(74) *Attorney, Agent, or Firm*—James D. Christoff

(57) ABSTRACT

Disclosed is an orthodontic article that includes a fluoropolymer and that exhibits at least 0.001% transmittance at 546 nm when measured according to the Transmittance Test Procedure.

21 Claims, 9 Drawing Sheets

OTHER PUBLICATIONS

Nakabayashi et al., "Preparation of Hard Tissue Compatible Materials: Dental Polymers," Biomedical Polymers, pp. 85–111 (1980).

Nakanishi et al., "Visible Light–Curable Tris[(meth)acryloyloxyalkyl] Isocyanurate Compositions," Pharmaceuticals 116:158986Z, p. 465 (1992).

Ozaki et al., "Laser–Raman Spectroscopic Study of the Adhesive Interface Between 4–MET/MMA–TBB Resin and Hydroxyapatite or Bovine Enamel," Dental Materials Journal 10(2):105–120 (1991).

Rowan et al., "Thermoplastic Fluoropolymers," Engineered Materials Handbook, vol. 2, pp. 115–119 (1988).

* cited by examiner-

FLUOROPOLYMERIC ORTHODONTIC ARTICLE

BACKGROUND OF THE INVENTION

This invention relates to fluoropolymeric orthodontic articles.

Orthodontic treatment often involves the application of mechanical forces to urge improperly positioned teeth into correct alignment. One common form of orthodontic treatment includes the use of orthodontic brackets affixed to the surface of a tooth, and a resilient curved arch wire seated in slots on the brackets. The arch wire exerts a restoring force on the teeth which tends to shift the teeth into orthodontically correct alignment.

Orthodontic articles such as, e.g., brackets, were traditionally formed from metal, but more recently have been formed from plastic and ceramic. Plastic brackets can be fabricated to be translucent to transparent in character relative to metal brackets. It is often difficult, however, to maintain the aesthetic characteristics of plastic brackets during use because food and beverages can stain and discolor the brackets while they reside in a patient's mouth.

SUMMARY OF THE INVENTION

In one aspect, the invention features an orthodontic article (e.g., an orthodontic bracket) that includes a fluoropolymer and that exhibits at least about 0.001% transmittance at 546 nm when measured according to the Transmittance Test Procedure described herein. In another embodiment, the article exhibits at least about 0.01% transmittance at 546 nm when measured according to the Transmittance Test Procedure. In other embodiments, the article exhibits a transmittance of at least about 0.001% over a wavelength range of from 400 nm to 800 nm when measured according to the Transmittance Test Procedure.

In one embodiment, the article exhibits a Delta E color shift of no greater than about 2 when tested according to the Hydrophilic Color Shift Test, and a Delta E color shift of no greater than about 5 when tested according to the Oleophilic Color Shift Test.

Suitable fluoropolymers are selected from the group consisting of perfluoroethylene-propylene copolymer, perfluoroalkoxyethylene, ethylene-tetrafluoroethylene copolymer, polyvinylidenefluoride, polyvinylfluoride, polychlorotrifluoroethylene, ethylene-chlorotrifluoroethylene copolymer, and combinations thereof. In one embodiment, the fluoropolymer includes perfluoroethylene-propylene copolymer. In another embodiment, the fluoropolymer includes perfluoroalkoxyethylene. In other embodiments, the fluoropolymer includes ethylene-chlorotrifluoroethylene copolymer.

The article may further include a polymeric composition disposed on a surface of the article, where the polymeric composition includes an organoborane compound. In another embodiment, the article further includes an organoborane amine complex disposed on a surface of the article.

In another aspect, the invention features a method for using an orthodontic bracket, where the method includes: (a) contacting a fluoropolymeric orthodontic bracket having an average transmittance of at least 0.001% when measured according to the Transmittance Test Method with a composition that includes an organoborane compound; and (b) adhering the bracket to a tooth. In one embodiment, the method further includes: contacting the surface that includes an organoborane compound with a polymerizable component; and polymerizing the polymerizable component to form an adhesive composition. In other embodiments, the method further includes contacting a polyimide film with the composition that includes the organoborane compound prior to adhering the bracket to a tooth.

In another embodiment, the method further includes treating the organoborane treated surface with a polymerizable component, and polymerizing the polymerizable component. In one embodiment, the method further includes contacting the polymerized component treated surface with an adhesive composition.

In another aspect the invention features an orthodontic article that includes a fluoropolymer selected from the group consisting of perfluoroethylene-propylene copolymer, perfluoroalkoxyethylene, ethylene-tetrafluoroethylene copolymer, polyvinylidenefluoride, polyvinylfluoride, polychlorotrifluoroethylene, ethylene-chlorotrifluoroethylene copolymer, and combinations thereof. In one embodiment, the orthodontic article includes a bracket. The orthodontic article may further include a metallic component.

In another aspect, the invention features a kit for adhering an orthodontic article to a tooth. The kit includes an orthodontic article that includes a fluoropolymer having at least about 0.001% transmittance at 546 nm when measured according to the Transmittance Test Procedure; and an adhesive system that includes a) a polymerizable component; and b) an organoborane amine complex. In one embodiment, the organoborane amine complex is disposed on a surface of the orthodontic article. In another embodiment, the kit further includes a polyimide film.

The orthodontic articles are resistant to staining by food and beverages such as mustard and spaghetti sauce such that the article remains aesthetically pleasing in appearance and does not unduly darken or turn yellow during the time the article remains in the oral cavity. The orthodontic articles also maintain their essentially translucent to transparent character over the useful life of the article such that they transmit the color of the underlying tooth surface to which they are adhered.

Other features and advantages of the invention will be apparent from the following description of the preferred embodiments thereof, and from the claims.

DESCRIPTION OF THE PREFERRED EMBODIMENTS

Orthodontic articles are capable of being mounted on a tooth, and are used to transmit to the tooth a corrective force from an arch wire, spring, elastic, or other activatible force-applying component.

Figure 1:
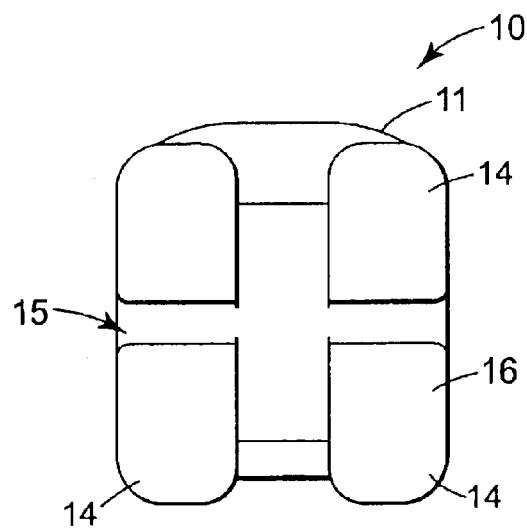
FIG. 1 is a front view looking toward a buccolabial side (i.e., toward a lip or cheek facing side) of an orthodontic bracket.
Figure 2:
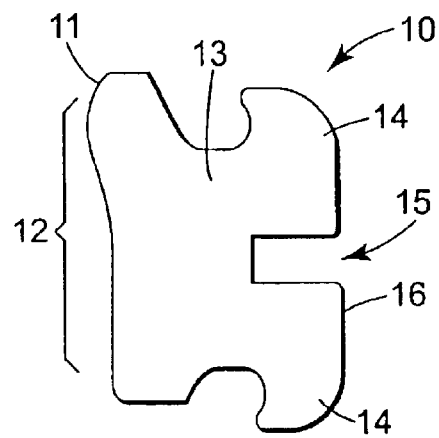
FIG. 2 is an end view of the orthodontic bracket of FIG. 1.

FIGS. 1 and 2 show an exemplary orthodontic article in the form of an orthodontic bracket 10. The bracket has a base 11 suitable for either direct bonding to a tooth or attachment to any kind of mounting fixture. A tooth facing surface 12 of the base 11 can be concavely curved about both mesiodistal axis and an apical axis to match the natural convexity of the tooth labial surface, but other curvatures or flat surfaces can also be used to accommodate bracket positioning. A bracket body 13 extends from base 11 to define bracket tie-wings 14 for ligature anchorage, and a mesiodistally oriented archwire slot 15 extending from an outer body surface 16 into the bracket body.

Figure 3:
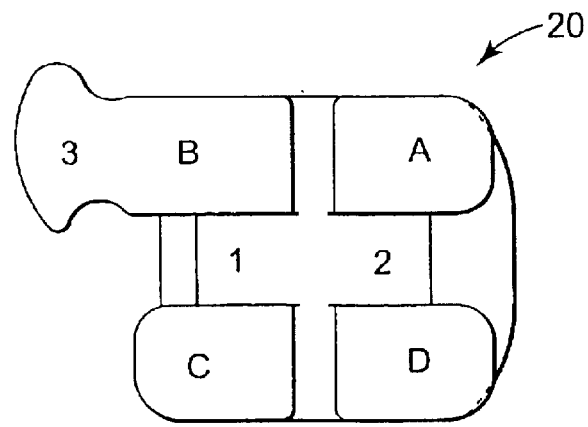
FIG. 3 is a front view looking toward a buccolabial side (i.e., toward a lip or cheek facing side) of a second embodiment of an orthodontic bracket.
Figure 4:
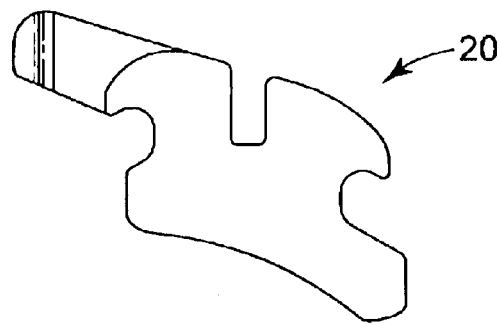
FIG. 4 is an end view of the orthodontic bracket of FIG. 3.
Figure 5:
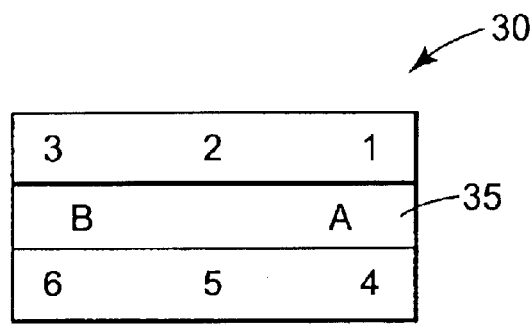
FIG. 5 is a front view of a third embodiment of a test article.
Figure 6:
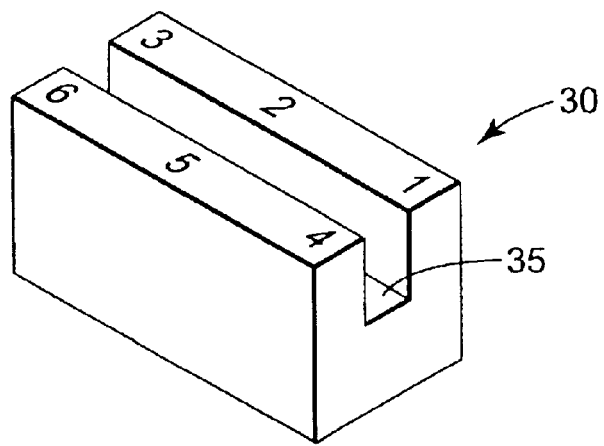
FIG. 6 is a perspective side view of the test article of FIG. 5.

FIGS. 3 and 4 depict a second embodiment of an orthodontic bracket 20 as seen from the buccolabial side and from the end, respectively. FIGS. 5 and 6 depict a test article 30 in which a slot 35 is seen from the top in FIG. 5. The article is shown in perspective side view in FIG. 6. The test article of FIGS. 5 and 6 approximates the overall size and thickness of a conventional orthodontic bracket.

The fluoropolymeric orthodontic articles described herein are resistant to staining during use such that the articles maintain their original color as determined by the unaided human eye under common lighting conditions (e.g., sunlight and incandescent light). The fluoropolymeric orthodontic articles are resistant to staining from oil-based staining agents such as, e.g., spaghetti sauce, and water-based staining agents such as, e.g., mustard. Preferably the fluoropolymeric orthodontic articles exhibit a Delta E color shift of less than 2 (more preferably less than 1, and most preferably 0) when tested according to the hydrophilic color shift test procedure set forth below, and a Delta E color shift of less than 5 (more preferably less than 3, and most preferably 0) when tested according to the oleophilic color shift test procedure set forth below.

The orthodontic articles appear translucent to transparent to the human eye such that when the article is placed on a surface such as, e.g., a tooth, the article transmits the color of the underlying surface through the article. Preferably the article exhibits at least about 0.001% transmittance at 546 nm, more preferably 0.01% transmittance at 546 nm when measured according to the Transmittance Test Procedure set forth below. Preferred articles exhibit a transmittance of at least about 0.001% over the wavelength range of 400 nm to 800 nm when measured according to the Transmittance Test Procedure.

The fluoropolymeric orthodontic articles include fluoropolymer resins that are capable of being hardened and have sufficient strength, hydrolytic stability, and non-toxicity to render them suitable for use in the mouth. The fluoropolymers are translucent to transparent. Preferred fluoropolymers exhibit at least about 0.001% transmittance, more preferably 0.01% transmittance, at 546 nm when measured according to the Transmittance Test Procedure. Useful fluoropolymers include perfluoroethylene-propylene copolymer, perfluoroalkoxyalkane, ethylene-tetrafluoroethylene copolymer, polyvinylidenefluoride, polyvinylfluoride, polyfluorotrifluoroethylene, ethylene-chlorotrifluoroethylene copolymer, and combinations thereof.

Examples of useful commercially available fluoropolymers include: Tefzel HT 2004 ethylene-tetrafluoroethylene copolymer including glass fibers, Tefzel 200, Tefzel 220, Tefzel 280, Tefzel 210, HT 2055, HT 2055NA, HT 2088NA, HT 2098, HT 2118, HT 2141, HT 2155 and HT 2158 ethylene-tetrafluoroethylene copolymers, Teflon PFA 340 perfluoroalkoxy fluorocarbon resin, and Teflon AF 1600 and Teflon AF 2400 perfluoro(2,2-dimethyl-1,3-dioxole)-tetrafluoroethylene copolymer (all available from DuPont); Hyflon PFA tetrafluoroethylene-perfluorovinylether copolymer, and Halar, Halar 300 and Halar 500 DA ethylene-chlorotrifluoroethylene copolymer (all available from Ausimont); Kel-F 81 PCTFE polychlorotrifluoroethylene (available from Minnesota Mining and Manufacturing), and the line of fluoropolymers available under the trade designation "THV" from Dyneon, LLC (Oakdale, Minn.).

Preferred adhesive systems for bonding a fluoropolymeric article to a tooth surface include a primer composition and a polymerizable component. The primer composition is capable of enabling or enhancing the adhesion of a fluoropolymeric article to the surface of a tooth. Usefull primer compositions include an organoborane amine complex capable of initiating polymerization of a polymerizable component. The polymerizable component may include, e.g., monomers, oligomers, and combinations thereof that are capable of polymerizing and thereby forming an adhesive composition.

Preferred adhesive systems also include an effective amount of a compound that is reactive with or will remove the amine portion of the organoborane amine complex so as to liberate the organoborane and thereby allow the organoborane to initiate polymerization of polymerizable components.

Examples of useful organoborane amine complexes and adhesive systems that include an organoborane amine complex are described, e.g., in U.S. Pat. No. 5,539,070 (Zharov et al.), U.S. Pat. No. 5,616,796 (Pocius et al.), U.S. Pat. No. 5,681,910 (Pocius), and U.S. Pat. No. 5,310,835 (Skoultchi et al.), and in WO 98/17694 and WO 97/07151, each of which is incorporated herein.

The fluoropolymeric orthodontic article, the tooth, or a combination thereof, can be treated (i.e., primed) with a primer composition prior to adhering the article to the tooth. One example of a useful priming composition is Transbond XT Light cure priming composition (Minnesota Mining and Manufacturing ("3"), St. Paul, Minn.). Other useful priming compositions are described in U.S. Pat. No. 5,558,516 (Horn et al.) and incorporated herein. The above-described organoborane amine adhesive compositions are also suitable priming compositions.

One example of a useful method for adhering the fluoropolymeric orthodontic article to the surface of a tooth includes contacting the orthodontic article with an adhesive composition and adhering the orthodontic article to the tooth surface. The method can include priming a surface, e.g., the surface of the tooth, the orthodontic article, and combinations thereof, with a priming composition prior to adhering the orthodontic article to the surface of the tooth. The surface can be primed with one or more priming compositions sequentially, simultaneously and in combinations thereof. In one preferred method, the surface is primed with a composition that includes an organoborane amine complex. In another preferred method, the surface can be pretreated, e.g., primed, and then packaged for later use as described, for example, in U.S. Pat. No. 5,558,516 (Hom et al.) and incorporated herein. After pretreatment, the surface can be treated with a primer composition, an adhesive composition and combinations thereof.

EXAMPLES

Transmittance Test Procedure

The % transmittance of light through an article is measured as follows. An article is placed in the well of a glass well slide such that the tooth contacting surface of the article is in contact with the slide. The well is filled with immersion liquid having a refractive index ("ND") of 1.515 and covered with a coverslip. The bracket containing slide is then placed under a microscope having a 3.2× objective, a numerical aperture ("N.A.") of 0.06, and a substage condensing lens system having a 0.3 N.A. The aperture and field diaphragms on the substage condensor are set up to produce the standard transparency by transmission measurement configuration (t(o/180)) of ASTM E-179-91a "Standard Guide for the Selection of Geometric Conditions for Measurement of Reflection and Transmission Properties of Materials."

The area of the article that is of interest is then brought into focus. The slide is then moved such that a reference area is brought into view (the focus of the microscope is not changed during this procedure). The reference area is an area within the well that contains immersion oil but does not contain the article. A calibration spectrum is collected from the reference area and is defined as having a transmittance of 1.0 over the wavelength range. The slide is then moved such that the area of interest of the article is brought into the field of view and the transmittance spectrum is collected over a predetermined wavelength or wavelength range e.g., 400 nm to 800 nm.

A series of measurements are taken at a number of locations on the article that are visible to an observer when the article is worn by a user, see, e.g., the numbers and letters indicated on FIGS. 3, 4, 5, 6 and 13. The measurements are taken in a labial-lingual direction along paths that extend from the labial-most surface of the article to the lingual-most base of the article, being careful to avoid areas in which a metal object is present in the article and would interfere with the path of the beam of radiation. The lowest transmittance value obtained for the article at a given wavelength is the transmittance of the article at that wavelength.

Color Measurement and Calculation Test procedure

The color shift in an article is measured as follows. A LABSPHERE certified diffuse white reflectance standard (CSS-99-010 8812A) is placed on the stage of a Leitz Orthoplan Microscope equipped with a Leitz MPV-SP Spectrophotometer illuminated with a tungsten halogen lamp. The microscope is set to 3.2× objective with a numerical aperture ("N.A.") of 0.06. A fiber optic ring, which produces a 45 degree cone of illumination, is mounted on the objective lens of the microscope producing a standard 45° illumination/ 0° detection color measurement (R(45/0)) according to ASTM E-179-91a, "Standard Guide for the Selection of Geometric Conditions for Measurement of Reflection and Transmission Properties of Materials."

The spectrophotometer is set to a measuring spot of 1 mm×1 mm, slit width of 6 nm, threshold of 1, high voltage of 480v, filter edge 100 Hz, and integration 8×. Two scans are taken from 370 nm to 800 nm at a sampling rate of ⅓ nm and data is reported every 1 nm.

The lamp intensity of the halogen lamp is adjusted such that the signal is never greater than 90% of that needed to saturate the detector. A calibration spectrum is collected from the area and is defined as having a reflectivity of 100% over the wavelength range. The reflectance standard is removed and a sample is placed on the microscope stage. An area of interest is brought into crisp focus and a reflectance spectrum is collected. The reflectance standard is returned to the microscope stage, brought into focus and the reflectance spectrum is collected. If the spectrum collected is other than 100% for the second measurement of the standard over the wavelength range, the standardization steps are repeated.

The color measurements and calculations are performed in accordance with ASTM standards E-308-95, "Standard Practice for Computing the Colors of Objects by Using the CIE System," and D 2244-93, "Standard Test Method for Calculation of Color Differences from Instrumentally Measured Color Coordinates" using the L*a*b* color representation. The L* value is a measure of the brightness of the sample. The a* is a measure of the redness for a positive value or greenness for a negative value, and b* is a measure of yellowness for a positive value or blueness for a negative value. Color differences (i.e., $\Delta L^*$, $\Delta a^*$ and $\Delta b^*$) are calculated by subtracting the reference value from the sample value. The total color shift is represented by delta E according to the following formula:

$$\Delta E = \sqrt{\Delta L^{*2} + \Delta a^{*2} + \Delta b^{*2}}$$

Hydrophilic Color Shift Test Procedure

The color shift exhibited by an article after contact with a hydrophilic substance is measured as follows. Specimens are immersed for one hour at 60° C. in French's 100% pure prepared yellow mustard. The samples are then removed, rinsed thoroughly with water, and air-dried.

The samples are then tested according to the above Color Shift Measurement and Calculation Test Procedure to determine Delta E.

Oleophilic Color Shift Test Procedure

The color shift exhibited by an article after contact with an oleophilic substance is measured as follows. Specimens are immersed for 2.5 hours at 60° C. in Ragu Old World Style Flavored Spaghetti sauce with meat. The samples are then removed, rinsed thoroughly with water, and air-dried. The samples are then tested according to the above Color Shift Measurement and Calculation Test Procedure to determine Delta E.

Staining Test Procedure

Example 1

A 1 cm×1 cm×3 mm sample of Ausimont PFA 450 perfluoroalkoxy fluorocarbon resin (Ausimont) was immersed in French's mustard for period of two weeks at 60° C. The sample was then removed, washed with water, dried and adhered onto a white paper chart. Visual observations regarding the degree of staining were made and recorded. The results are summarized in Table I.

Additional samples of the Ausimont PFA 450 were immersed in either Ragu spaghetti sauce, chili powder (Spice Island) at 1 g per 10 g water, or curry powder (Shilling) at 1 g per 10 g water. The samples remained in the staining agents for two weeks at 60° C. After two weeks the samples were removed, washed with water, and adhered to a chart. Visual observations regarding the degree of staining were made and recorded. The results are summarized in Table I.

Example 2

1 cm×1 cm×3 mm samples of Ausirnont Halar polyethylene-chlorine trifluoroethylene were stain tested as in Example 1. No staining was observed.

Example 3

1 cm×1 cm×3 mm samples of DuPont PFA 340 perfluoroalkoxy fluorocarbon resin (DuPont) were stain tested as in Example 1. No staining was observed.

Example 4

1 cm×1 cm×3 mm samples of Tefzel 210 ethylene-tetrafluoroethylene (DuPont) were stain tested as in Example 1. No staining was observed for the samples immersed in spaghetti sauce, mustard, and chili. A very light yellow was observed for the sample immersed in curry.

Example 5

1 cm×1 cm×3 mm samples of Tefzel 280 ethylene-tetrafluoroethylene (DuPont) were stain tested as in Example 1. No staining was observed.

The results obtained in Examples 1–5 are summarized in Table I.

TABLE I

| Sample | Spaghetti Sauce | Mustard | Chili | Curry |
| --- | --- | --- | --- | --- |
| Example 1 | None | None | None | None |
| Example 2 | None | None | None | None |
| Example 3 | None | None | None | None |
| Example 4 | None | None | None | v. Light yellow |
| Example 5 | None | None | None | None |

Bond Strength Test Method

Samples are adhered to a knurled steel ring and immersed in a 37° C. water bath for 16–24 hours. The ring with bonded samples is removed from the water, air-dried, and then placed onto the test fixture of an Instron Universal tensile test equipment. A wire loop is placed into the upper jaw of the test fixture and through the sample such that it is affixed to the sample. The wire is then pulled by the upper jaw of the test fixture at a rate of 0.2 inches per minute (0.5 cm/min) at a full scale load of 100 lbs (45 kg). The bond strength (in pounds) at separation of the sample from the metal ring is recorded.

Primer Composition Preparation

A primer composition was prepared by combining:

3.5 parts by weight of a monomer mixture of 39 parts by weight methyl methacrylate, 28 parts by weight butyl acrylate, 3 parts by weight methacrylic acid, 30 parts by weight poly(methylmethacrylate-co-ethyl acrylate (mol. wt. 101,000 (Aldrich)), and 100 parts by weight of a complex of triethylborane and Dytek A 2-methyl-1,5-pentane diamine, having one equivalent of boron per equivalent of nitrogen, and mixing with a wooden stick.

Sample Preparation

Example 6

The 0.231 cm×0.330 cm surface of a 0.231 cm×0.330 cm×0.183 cm embossed cube of Halar 500DA ethylene-chlortrifluoroethylene copolymer (available from Ausimont U.S.A. Inc.) was dipped into the above-described-primer composition such that the primer composition completely covered the surface. The primed surface was then pressed against a grooved, knurled steel bonding ring, such that the cube adhered to the bonding ring, and the primer composition was allowed to cure for 48 hours.

The cube was then tested according to the Bond Strength Test Method. The results are reported in Table II.

Example 7

A dab of primer composition prepared as described above was coated onto a polyimide film. The 0.231 cm×0.330 cm surface of a 0.231 cm x 0.330 cm×0.183 cm embossed cube of Halar 500DA ethylene-chlortrifluoroethylene copolymer (Ausimont) was dipped into the primer composition such that a face of the cube was completely covered with the primer composition. The primer composition was allowed to cure for 48 hours, after which the cube was peeled from the polyimide film. Transbond XT light cure primer composition (3M) was then applied to the primed surface of the cube. The Transbond XT primer was allowed to sit for 60 seconds and then cured with visible light. The primed surface was then coated with Transbond XT light cure adhesive composition (3M), and adhered to a knurled steel bonding ring. The Transbond XT adhesive was then cured by exposing the Transbond XT adhesive to radiation emitted from an Ortholux XT Visible Light Curing Unit for 10 seconds.

The bonded cube was then tested according to the Bond Strength Test Method. The results are reported in Table II.

Example 8

The 0.231 cm×0.330 cm surface of a 0.231 cm×0.330 cm×0.183 cm cube of Halar 500DA ethylene-chlortrifluoroethylene copolymer (Ausimont) was primed and adhered to a grooved, knurled steel ring according to the method set forth in Example 6.

The bonded cube was then tested according to the Bond Strength Test Method. The results are reported in Table II.

Example 9

The 0.231 cm×0.330 cm surface of a 0.231 cm×0.330 cm×0.183 cm cube of Halar 500DA ethylene-chlortrifluoroethylene copolymer (Ausimont) was primed and adhered to a grooved, knurled steel ring according to the method set forth in Example 7.

The bonded cube was then tested according to the Bond Strength Test Method. The results are reported in Table II.

Example 10

A base surface of a test sample in a form depicted in FIGS. 5 and 6 made from Teflon PFA340 perfluoroalkoxy fluorocarbon resin (DuPont) was primed and adhered to a grooved, knurled steel ring according to the method set forth in Example 6. The test sample was then tested according to the Bond Strength Test Method. The results are reported in Table II.

Example 11

A base surface of a test sample in a form depicted in FIGS. 5 and 6 made from Teflon PFA340 was primed and adhered to a grooved, knurled steel ring according to the method set forth in Example 7. The bonded bracket was then tested according to the Bond Strength Test Method. The results are reported in Table II.

For Examples 6–11, the bond strength ranged from 7 to 23 pounds ("lbs")/sample with an average of 16 lbs/sample. The failure mode was adhesive between the primer composition and the sample (i.e., the cube or the test sample).

TABLE II

| Example | Bond Strength (lbs) | Standard Deviation |
|---------|---------------------|--------------------|
| 6       | 22                  | 3.0                |
| 7       | 5                   | 1.4                |
| 8       | 20                  | 5.4                |
| 9       | 10                  | 3.9                |
| 10      | 13                  | 5.3                |
| 11      | 6                   | 2.7                |

Example 12

Figure 7:
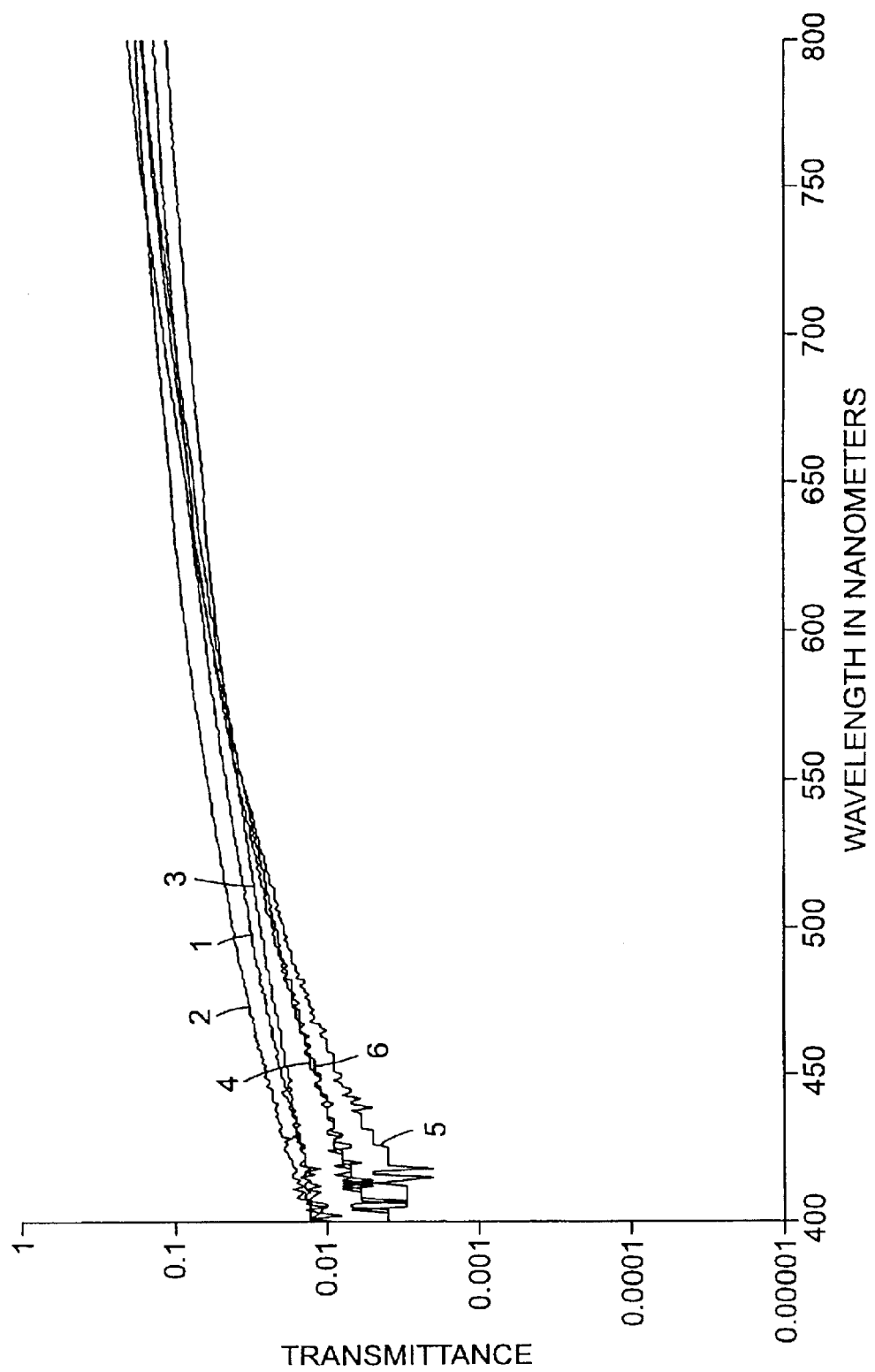
FIG. 7 is a plot of % transmittance versus wavelength (nm) for the bracket of Example 12.

A test sample formed from virgin Halar ethylene-chlorotrifluoroethylene copolymer (Ausimont), having a shape as depicted in FIGS. 5 and 6, was tested according to the Transmittance Test Procedure set forth above. Transmittance was measured through regions identified as 1, 2, 3, 4, 5 and 6 in FIG. 5. The results are shown in % transmittance versus wavelength (nm) in FIG. 7.

Example 13

Figure 8:
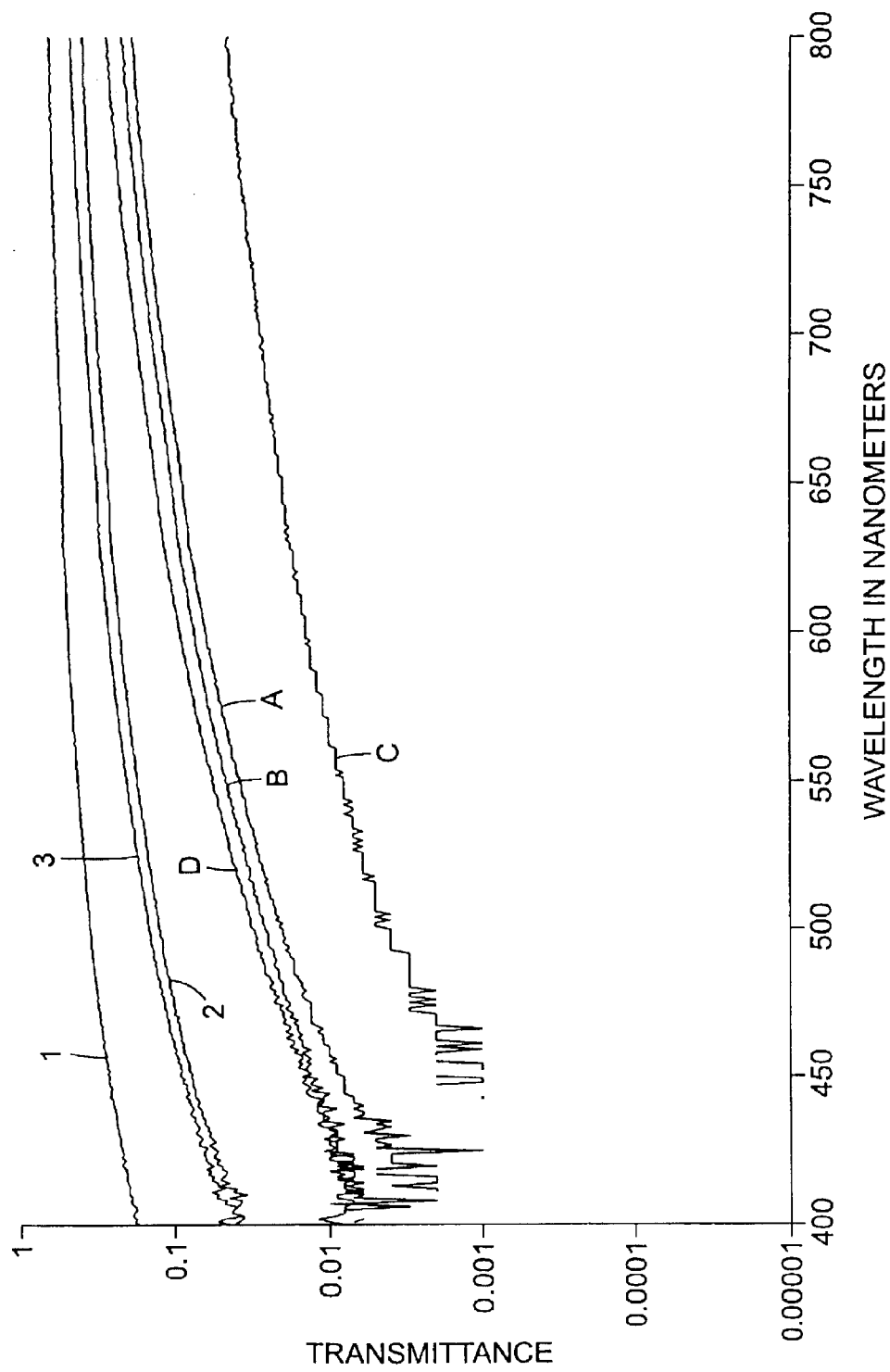
FIG. 8 is a plot of % transmittance versus wavelength (nm) for the bracket of Example 13.

A bracket made from Halar ethylene-chlorotrifluoroethylene copolymer (Ausimont), having a shape as depicted in FIGS. 3 and 4, was tested according to the Transmittance Test Procedure set forth above. Transmittance data was obtained at locations identified as A, B, C, D, 1, 2 and 3 on FIG. 3. The results are shown in % transmittance versus wavelength (nm) in FIG. 8.

Example 14

Figure 9:
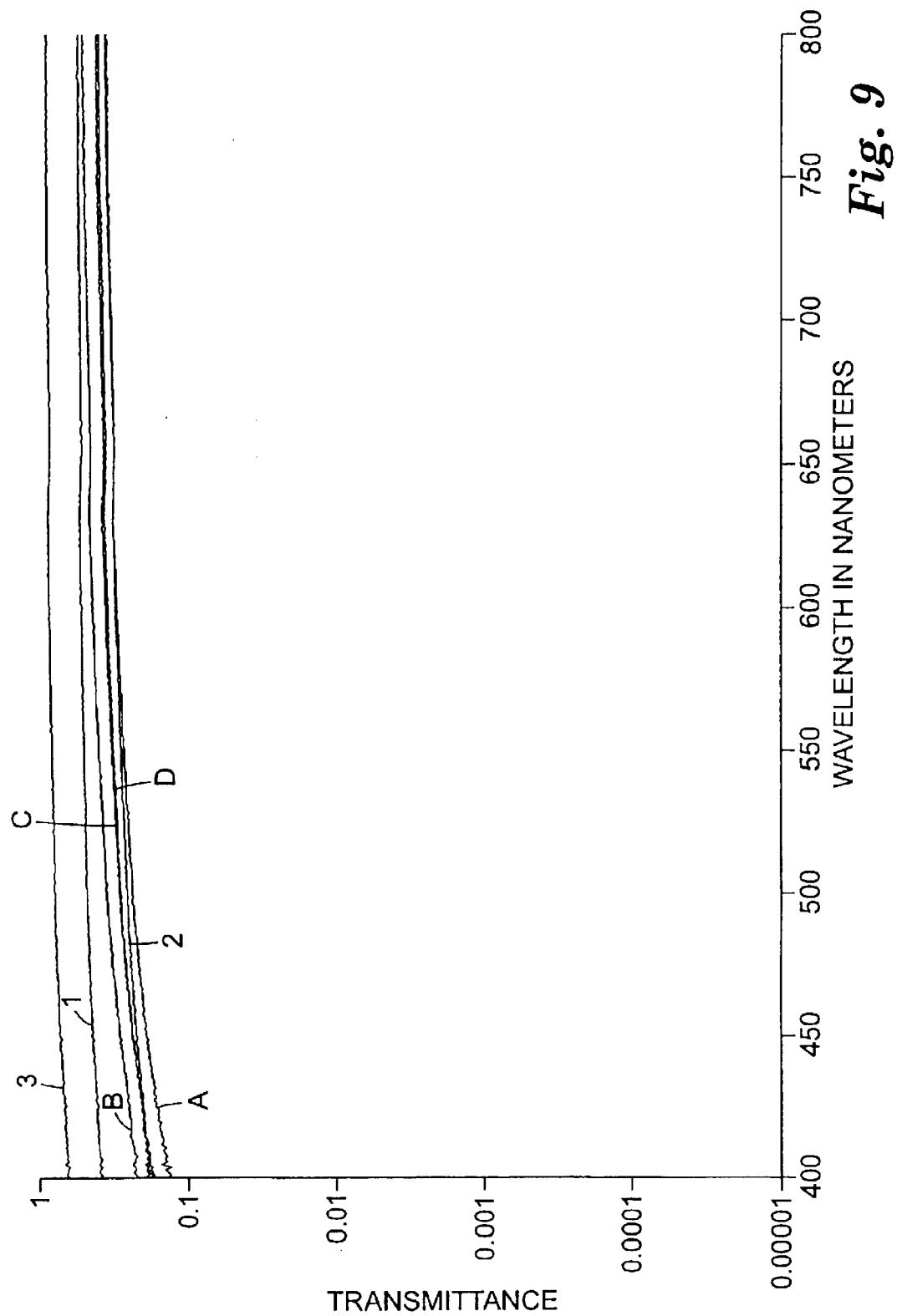
FIG. 9 is a plot of % transmittance versus wavelength (nm) for the bracket of Example 14.

A bracket made from Teflon PFA tetrafluoroethylene-perfluorovinylether copolymer (DuPont), having a shape as depicted in FIGS. 3 and 4, was tested according to the Transmittance Test Procedure set forth above. Transmittance data was obtained at locations identified as A, B, C, D, 1, 2 and 3 in FIG. 3. The results are shown in % transmittance versus wavelength (nm) in FIG. 9.

Example 15

Figure 10:
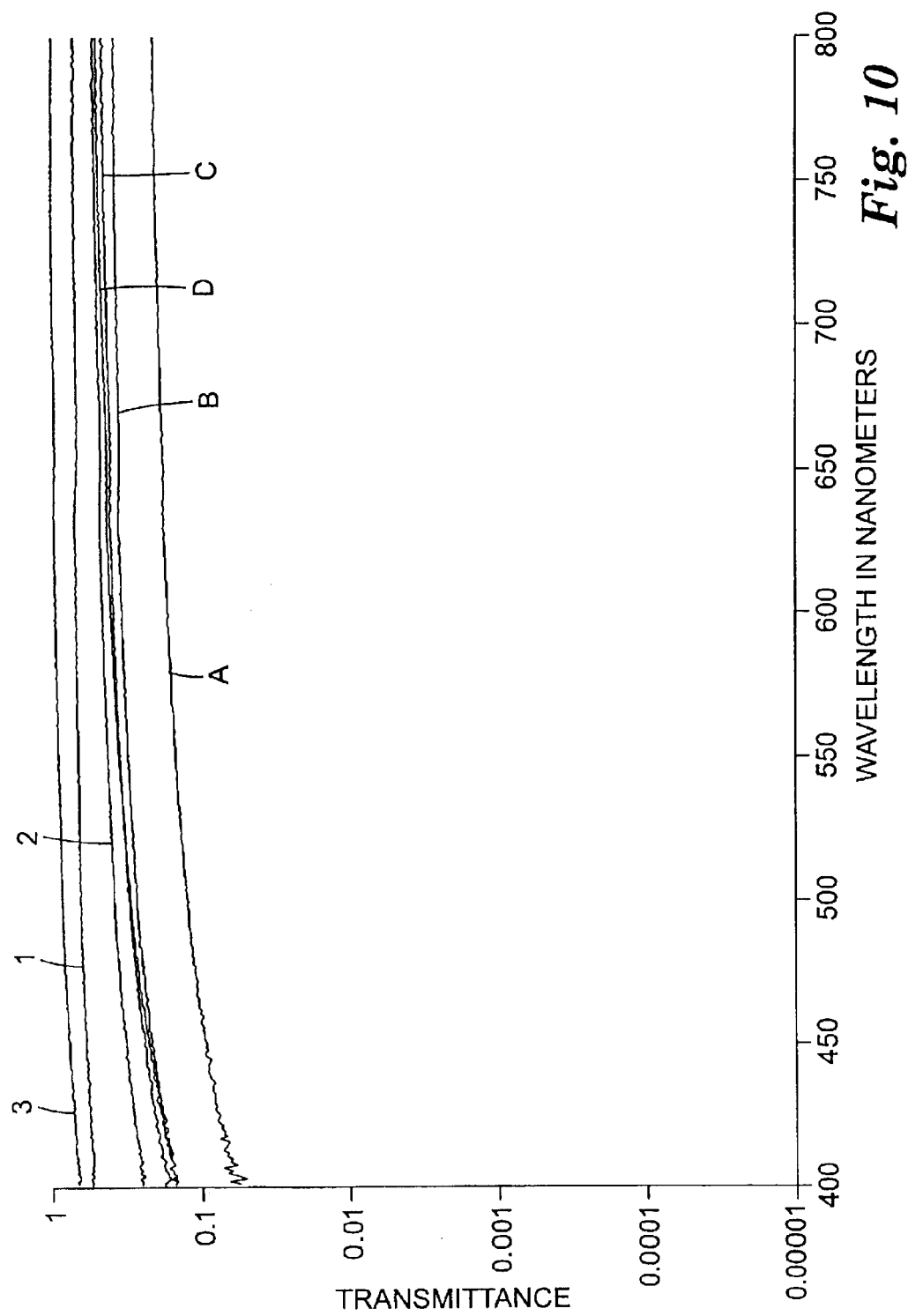
FIG. 10 is a plot of % transmittance versus wavelength (nm) for the bracket of Example 15.
Figure 13:
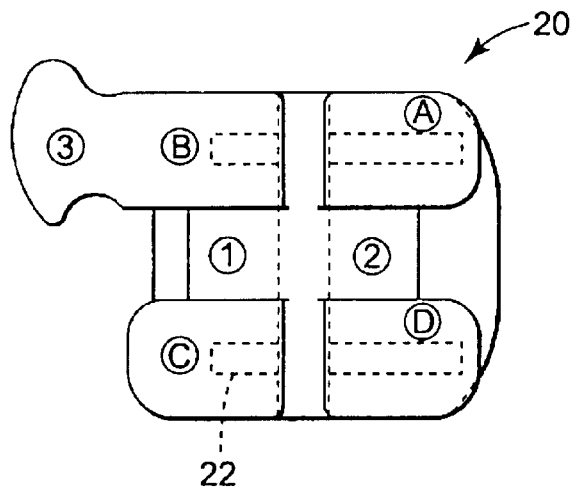
FIG. 13 is a front view looking toward a buccolabial side of an embodiment of an orthodontic bracket that includes a metallic framework.

A bracket made from Teflon PFA tetrafluoroethylene-perfluorovinylether copolymer (DuPont) having a shape similar to the shape depicted in FIGS. 3 and 4 but with an embedded metallic framework as depicted in FIG. 13, was tested according to the Transmittance Test Procedure set forth above. Transmittance data was obtained at locations identified as A, B, C, D, 1, 2 and 3 in FIG. 13. The results are shown in % transmittance versus wavelength (nm) in FIG. 10.

Example 16

Figure 11:
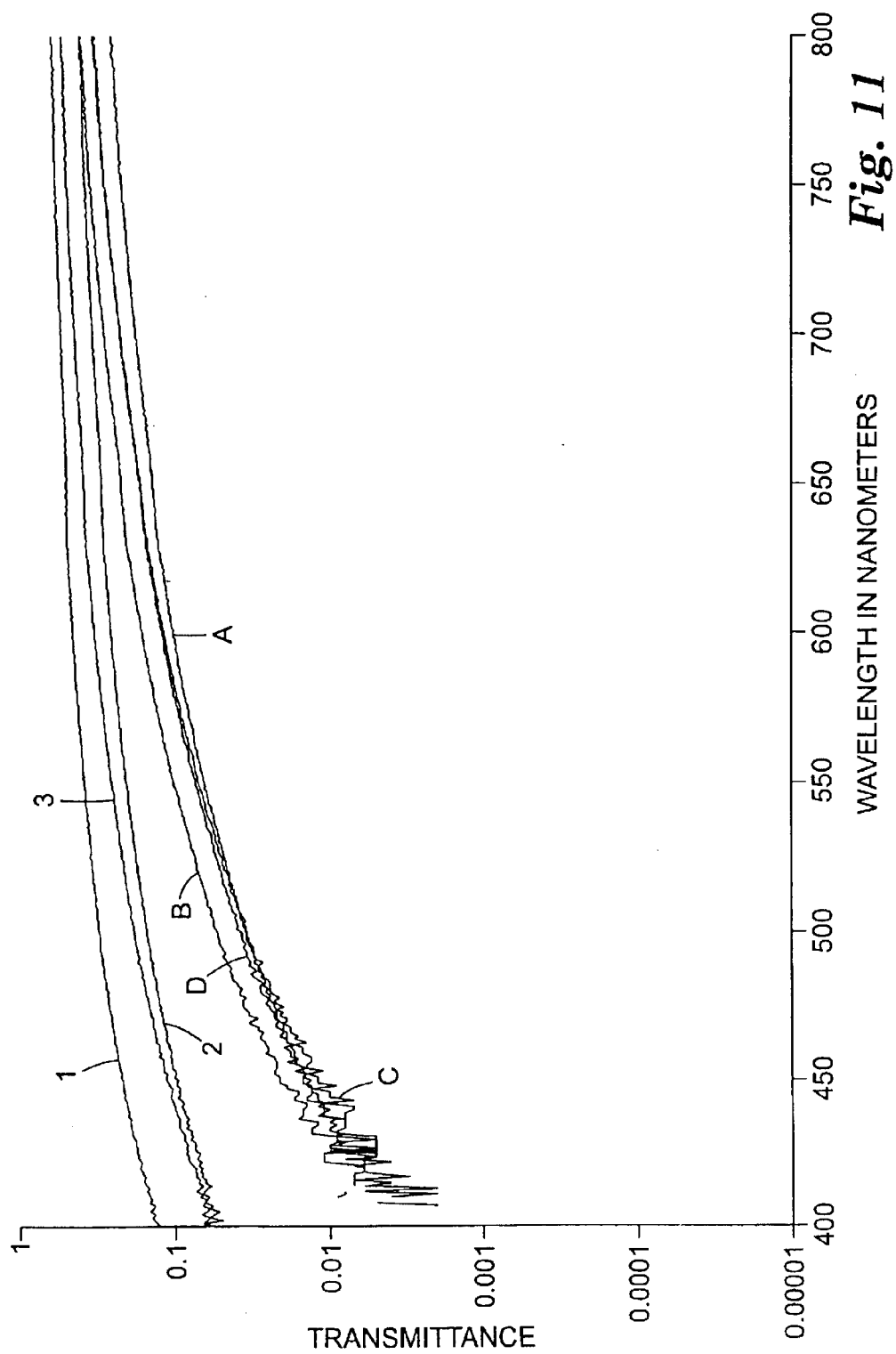
FIG. 11 is a plot of % transmittance versus wavelength (nm) for the bracket of Example 16.

A bracket made from Tefzel 210 ethylene-tetrafluorocthylene copolymer (available from DuPont), having a shape as depicted in FIGS. 3 and 4, was tested according to the Transmittance Test Procedure set forth above. Transmittance data was obtained at locations identified as A, B, C, D, 1, 2 and 3 in FIG. 3. The results are shown in % transmittance versus wavelength (nm) in FIG. 11.

Comparative Example 1

Figure 12:
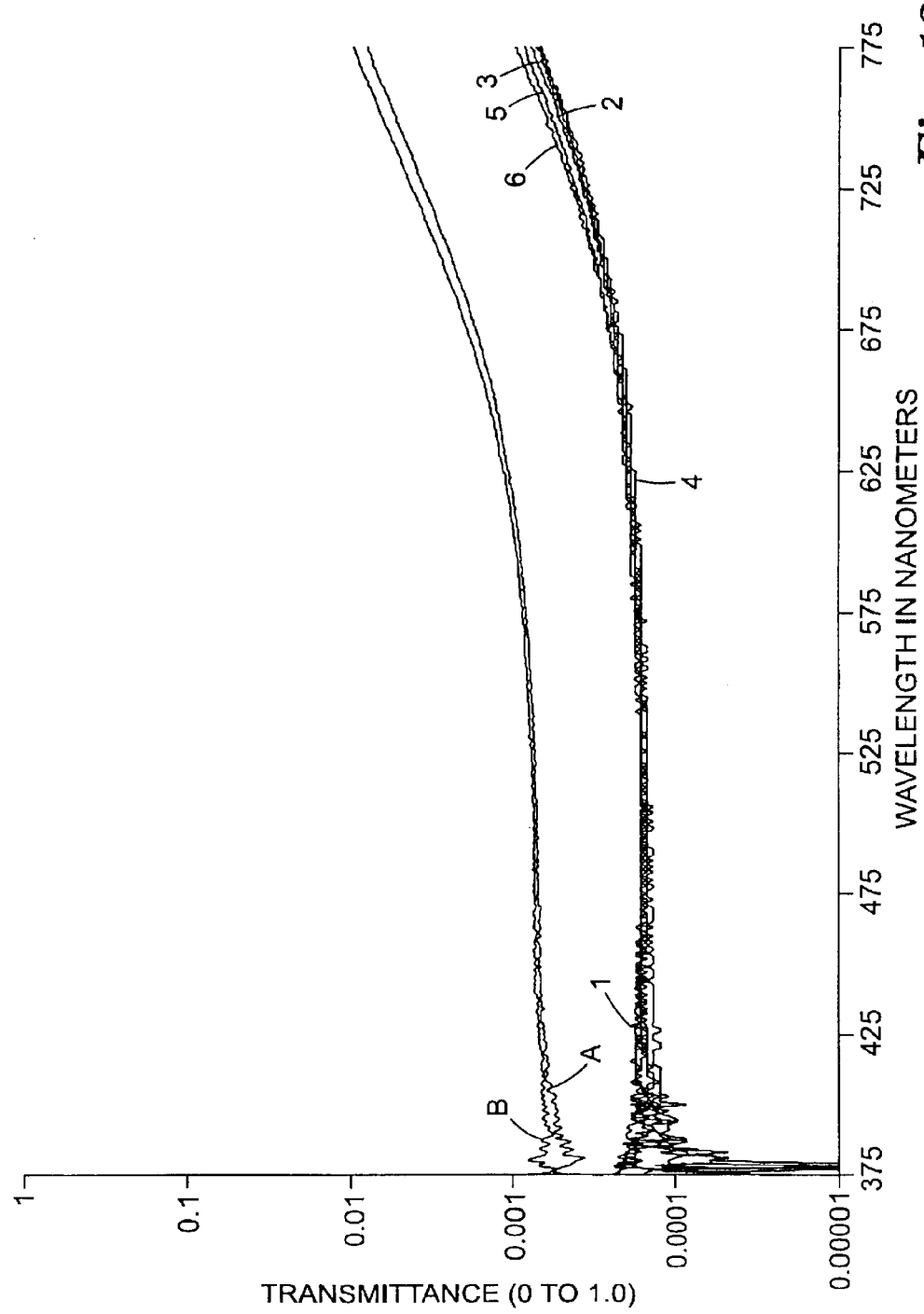
FIG. 12 is a plot of % transmittance versus wavelength (nm) for the bracket of Comparative Example 1.

A test article made from Teflon® polytetrafluoroethylene (available from DuPont), having a shape as depicted in FIGS. 5 and 6, was tested according to the Transmittance Test Procedure set forth above. Transmittance data was obtained at locations identified as A, B, 1, 2, 3, 4, 5 and 6 in FIG. 5. The results are shown in % transmittance versus wavelength (nm) in FIG. 12.

Other embodiments are within the claims. For example, the article can be pretreated with a polymerization initiator including, e.g., the above-described organoborane amine complexes, and packaged in a suitable package, e.g., a kit. The articles that have been pretreated with a polymerization initiator can also be provided with an adhesive precoat and packaged in a suitable package that optionally includes other components necessary to form an adhesive composition.

Figure 14:
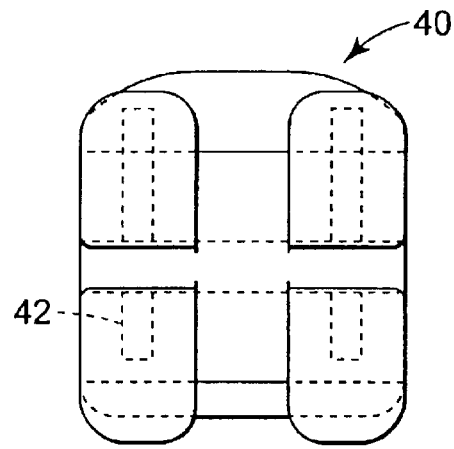
FIG. 14 is a front view looking toward a buccolabial side of another embodiment of an orthodontic bracket that includes a metallic framework.
Figure 15:
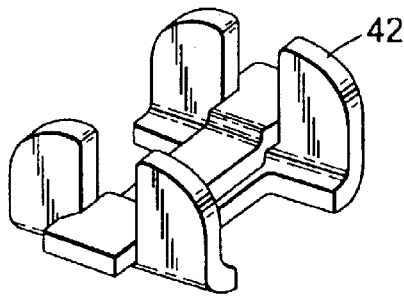
FIG. 15 is a perspective view of the metallic framework of FIG. 14.

The article may include a metallic component, e.g., a framework. Orthodontic brackets 20 and 40 including a metal framework 22, 42 depicted by dotted lines are shown in FIGS. 13 and 14. One embodiment of a metallic framework 42 is shown in perspective view in FIG. 15. The metallic framework 22, 42 may be partially or wholly embedded in the body of the bracket 20, 40. The framework can be coated or otherwise colored, e.g., by ink, paint, or porcelain, to match the color of the tooth or the color of the fluoropolymeric material. Examples of a metallic framework are described in U.S. Pat. No. 5,597,302 (Pospisil et al.), which is incorporated herein.

Figure 16:
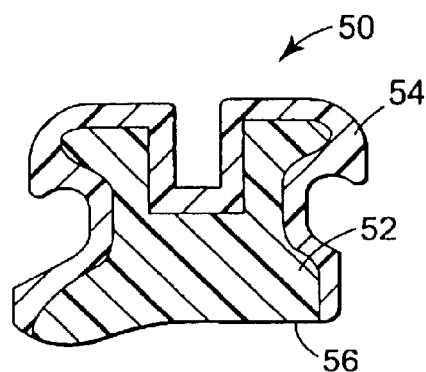
FIG. 16 is a side view of another embodiment of an orthodontic bracket that includes a fluoropolymeric layer on a nonfluoropolymeric interior.

The article may also include a nonfluoropolymeric interior and a fluoropolymeric exterior layer. The fluoropolymeric exterior layer may extend over the entire surface of the nonfluoropolymeric interior or a portion thereof. Examples of suitable nonfluoropolymeric materials include glass, ceramic, plastic (e.g., polycarbonate and polyurethane), or a combination thereof. One example of such an article would include a polycarbonate bracket having an exterior fluoropolymeric layer, and, optionally, an exposed polycarbonate surface, which can be used for bonding the bracket to a tooth. Referring to FIG. 16, an orthodontic bracket 50 having a nonfluoropolymeric interior 52 and a fluoropolymeric layer 54 surrounding a portion of the nonfluoropolymeric interior 52 is shown. Surface 56 of nonfluoropolymeric interior 52 is exposed and is available for bonding to a tooth.

All of the patents, patent applications and test methods cited above are incorporated by reference into this document in total.

What is claimed is:

1. An orthodontic bracket comprising a fluoropolymer, said bracket exhibiting at least about 0.001% transmittance at 546 nm when measured according to the Transmittance Test Procedure.

2. The bracket of claim 1, wherein said bracket exhibits a transmittance of at least about 0.001% over a wavelength range of from 400 nm to 800 nm when measured according to the Transmittance Test Procedure.

3. The bracket of claim 1, wherein said bracket exhibits a Delta E color shift of no greater than about 2 when tested according to the Hydrophilic Color Shift Test, and a Delta E color shift of no greater than about 5 when tested according to the Oleophilic Color Test.

4. The bracket of claim 1, wherein said fluoropolymer is selected from the group consisting of perfluoroethylene-propylene copolymer, perfluoroalkoxyethylene, ethylene-tetrafluoroethylene copolymer, polyvinylidenefluoride, polyvinylfluoride, polychlorotrifluoroethylene, ethylene-chlorotrifluoroethylene copolymer, or a combination thereof.

5. The bracket of claim 1, wherein said fluoropolymer comprises perfluoroethylene-propylene copolymer.

6. The bracket of claim 1, wherein said fluoropolymer comprises perfluoroalkoxyethylene.

7. The bracket of claim 1, wherein said fluoropolymer comprises ethylene-chlorotrifluoroethylene copolymer.

8. The bracket of claim 1, further comprising a polymeric composition disposed on a surface of said bracket, said polymeric composition comprising an organoborane compound.

9. The bracket of claim 1, wherein said bracket exhibits at least about 0.01% transmittance at 546 nm when measured according to the Transmittance Test Procedure.

10. The bracket of claim 1, further comprising an organoborane amine complex disposed on a surface of said bracket.

11. A method for using an orthodontic bracket, said method comprising:
    contacting an orthodontic bracket comprising a fluoropolymer and having an average transmittance of at least 0.001% when measured according to the Transmittance Test Method with a composition comprising an organoborane compound; and
    adhering said bracket to a tooth.

12. The method of claim 11, wherein said orthodontic bracket exhibits a Delta E color shift of no greater than about 2 when tested according to the Hydrophilic Color Shift Test, and a Delta E color shift of no greater than about 5 when tested according to the Oleophilic Color Shift Test.

13. The method of claim 11, wherein said fluoropolymer comprises a fluoropolymer selected from the group consisting of perfluoroethylene-propylene copolymer, perfluoroalkoxyethylene, ethylene-tetrafluoroethylene copolymer, polyvinylidenefluoride, polychlorotrifluoroethylene, ethylene-chlorotrifluoroethylene copolymer, or a combination thereof.

14. The method of claim 11, further comprising
    contacting said surface comprising an organoborane compound with a polymerizable composition; and
    polymerizing said polymerizable composition to form an adhesive composition.

15. The method of claim 11, further comprising
    contacting a polyimide film with said composition comprising an organoborane compound prior to adhering said bracket to a tooth.

16. An orthodontic article comprising a fluoropolymer selected from the group consisting of perfluoroethylene-propylene copolymer, perfluoroalkoxyethylene, ethylene-tetrafluoroethylene copolymer, polyvinylidenefluoride, polyvinylfluoride, polychlorotrifluoroethylene, ethylene-chlorotrifluoroethylene copolymer, or a combination thereof, wherein said article comprises a bracket.

17. The article of claim 16, further comprising a metallic component.

18. The article of claim 16, wherein said article exhibits a Delta E color shift of no greater than about 2 when tested according to the Hydrophilic Color Shift Test, and a Delta E color shift of no greater than about 5 when tested according to the Oleophilic Color Shift Test.

19. The article of claim 16, wherein said article exhibits at least about 0.001% transmittance at 546 nm when measured according to the Transmittance Test Procedure.

20. The article of claim 16, wherein said article exhibits at least about 0.01% transmittance at 546 when measured according to the Transmittance Test Procedure.

21. The article of claim 16, wherein said article exhibits at least about 0.001% transmittance over a wavelength range of from 400 nm to 800 nm when measured according to the Transmittance Test Procedure.

* * * * *

UNITED STATES PATENT AND TRADEMARK OFFICE
CERTIFICATE OF CORRECTION

PATENT NO. : 6,799,966 B1
DATED : October 5, 2004
INVENTOR(S) : Horn, Jerold S.

It is certified that error appears in the above-identified patent and that said Letters Patent is hereby corrected as shown below:

Column 2,
Line 2, after "least" insert -- about --.

Column 5,
Line 1, delete "("3")" and insert -- ("3M") --, therefor.
Line 19, delete "Hom" and insert -- Horn --, therefor.

Column 7,
Line 22, delete "Ausirnont" and insert -- Ausimont --, therefor.

Column 10,
Line 8, delete "tetrafluorocthylene" and insert -- tetrafluoroethylene --, therefor.

Column 12,
Line 38, after "546" insert -- nm --.

Signed and Sealed this

Eighteenth Day of January, 2005

JON W. DUDAS
*Director of the United States Patent and Trademark Office*